US009157633B2

(12) United States Patent
Akiyama et al.

(10) Patent No.: US 9,157,633 B2
(45) Date of Patent: Oct. 13, 2015

(54) METHOD FOR SUPPRESSING ADHESION OF ASH AND DEVICE FOR SUPPRESSING ADHESION OF ASH IN BOILER

(75) Inventors: Katsuya Akiyama, Kobe (JP); Haeyang Pak, Kobe (JP)

(73) Assignee: Kobe Steel, Ltd., Hyogo (JP)

( * ) Notice: Subject to any disclaimer, the term of this patent is extended or adjusted under 35 U.S.C. 154(b) by 804 days.

(21) Appl. No.: 13/382,182

(22) PCT Filed: Jul. 22, 2010

(86) PCT No.: PCT/JP2010/062379
§ 371 (c)(1),
(2), (4) Date: Jan. 4, 2012

(87) PCT Pub. No.: WO2011/010704
PCT Pub. Date: Jan. 27, 2011

(65) Prior Publication Data
US 2012/0107751 A1    May 3, 2012

(30) Foreign Application Priority Data
Jul. 22, 2009  (JP) .................................. 2009-170771

(51) Int. Cl.
*F23K 1/00* (2006.01)
*F23J 9/00* (2006.01)
(Continued)

(52) U.S. Cl.
CPC ... *F23K 1/00* (2013.01); *F23J 9/00* (2013.01); *F23N 1/002* (2013.01); *G01N 33/222* (2013.01);
(Continued)

(58) Field of Classification Search
CPC .... C04B 18/06; C04B 18/065; C04B 18/067; F23J 7/00; F23J 9/00; F23L 7/007; F23K 1/00; F23K 1/002; F23K 2201/1003; F23K 2201/501; F23K 2203/104; G01N 33/222; F23N 2037/08; F23N 2021/10
USPC ............. 431/3, 12, 29, 62; 110/186, 342, 327
See application file for complete search history.

(56) References Cited

U.S. PATENT DOCUMENTS

2001/0037703 A1* 11/2001 Fuji et al. .......................... 75/483

FOREIGN PATENT DOCUMENTS

JP          60-2119       1/1985
JP        09-250708       9/1997
(Continued)

OTHER PUBLICATIONS

International Search Report for PCT/JP2010/062379 mailed Oct. 12, 2010.
(Continued)

*Primary Examiner* — Alfred Basichas
(74) *Attorney, Agent, or Firm* — Studebaker & Brackett PC

(57) ABSTRACT

In order to stably operate a boiler using several kinds of solid fuels including depleted ash as fuels, adhesion of ash is suppressed. A calculator (9) preliminarily collects properties of a solid fuel, such as the content rate of ash and the composition of an ash constituent, as data (8). The calculator (9) uses the mix ratio of solid fuels as a parameter and calculates the composition of an ash constituent of the mixed fuels on the basis of the preliminarily measured composition of the ash constituent of each solid fuel. The calculator (9) determines a reference value of the rate of slug by which the ash deposition ratio is reduced on the basis of the relationship between the preliminarily measured ash deposition ratio and the slag ratio. Further, the calculator (9) calculates the mix ratio of each solid fuel using a thermodynamic equilibrium calculation so as to obtain an ash composition in which the slag ratio is not more than the determined reference value. On the basis of the mix ratio of each solid fuel calculated by the calculator (9), the amount of solid fuel dispensed from hoppers (1, 2) is adjusted by a fuel supply amount adjusting device (3). Thus, each solid fuel, the dispensed amount of which has been adjusted, is mixed by a mixer (4) and crushed by a crusher (5) before being supplied to a boiler (7) as a fuel and burned by a burner (6).

6 Claims, 3 Drawing Sheets

(51) Int. Cl.
*F23N 1/00* (2006.01)
*G01N 33/22* (2006.01)

(52) U.S. Cl.
CPC ... *F23K 2201/1003* (2013.01); *F23K 2201/501* (2013.01); *F23K 2203/104* (2013.01); *F23N 2021/10* (2013.01); *F23N 2037/08* (2013.01)

(56) References Cited

FOREIGN PATENT DOCUMENTS

| JP | 2004-361368 | | 12/2004 |
|---|---|---|---|
| JP | 2006-084062 | | 3/2006 |
| JP | 2006152331 | * | 6/2006 |
| WO | WO2011/010704 | | 1/2011 |

OTHER PUBLICATIONS

Office Action from Japanese Patent Office with corresponding Japanese Patent Application No. 2009-170771 mailed Mar. 26, 2013.

Gordon Couch, Understanding Slagging and Fouling During pf Combustion (IEACR/72), 1994, p. 64.

* cited by examiner

METHOD FOR SUPPRESSING ADHESION OF ASH AND DEVICE FOR SUPPRESSING ADHESION OF ASH IN BOILER

TECHNICAL FIELD

The present invention relates to a method for suppressing adhesion of ash and a device for suppressing adhesion of ash in a boiler using a solid fuel as a fuel.

BACKGROUND ART

Conventionally, a solid fuel crushed by a crusher is supplied as a fuel by conveyance air to a boiler using a solid fuel as a fuel. The boiler includes a furnace for generating heat by burning the supplied fuel by a burner or the like and heat exchange tube banks arranged from an upper part of the furnace toward a downstream side and adapted to carry out heat exchange by causing a combustion gas to flow inside. The combustion gas discharged from the boiler is exhausted from a chimney. Here, the heat exchange tube banks are composed of an upper heat transfer unit including a secondary heater, a tertiary heater, a final heater and a secondary reheater arranged side by side at predetermined intervals in an upper part of the furnace and a rear heat transfer unit includes a primary heater, a primary reheater and a coal economizer arranged in a rear part of the furnace.

Since ash is produced from burned coal in such a boiler, the ash flows due to the combustion gas in the boiler, and causes slagging and fouling in which the ash adheres to and deposits on wall surfaces of the furnace and the heat exchange tube banks arranged from the upper part of the furnace toward the downstream side while being exhausted. If such slagging and fouling occur, heat transfer surfaces of the heat exchange tubes are covered to drastically reduce heat absorption efficiency. Further, if a huge clinker is produced on the wall surface or the like due to slagging and fouling, and the clinker falls down, problems such that a furnace pressure drastically changes, the heat exchange tube at the furnace bottom is damaged, and the furnace bottom is closed is arised. Further, since the elements of the upper heat transfer unit provided in the upper part of the furnace are arranged at narrow intervals, the furnace pressure may largely change if ash deposits. Further, the ash adhering between the heat exchange tubes grows to close a gas flow path, with the result that the combustion gas may not be able to pass, thereby causing an operational failure. Further, since the temperature of the vicinity of the wall surfaces of the furnace is high due to radiation heat of combustion flames near the burner, the ash is likely to adhere to and melt on the heat exchange tube banks having relatively low temperatures, which causes a problem that a huge clinker is likely to grow.

Accordingly, to stably operate the boiler, it is necessary to avoid the occurrence of problems caused by adhesion of ash by predicting a possibility of adhesion of ash caused by burning the solid fuel in advance. Thus, it is being attempted to indicate the possibility of adhesion of ash as an index.

For example, in non-patent literature 1, a method is used which predicts a possibility of adhesion of ash in advance based on an ash-related index based on an ash composition expressing ash containing elements in the form of oxides and an evaluation criterion. However, the index and the evaluation criterion shown in non-patent literature 1 are intended for bituminous coal, which is good quality coal with fewer problems such as adhesion of ash. As just described, since non-patent literature 1 is not intended for poor quality coals (e.g. subbituminous coal, lignite, high-silica coal, high-calcium coal and other coal types), the demand for which increases recently, there is a problem that the relationship of index and adhesion of ash disclosed in non-patent literature 1 does not necessarily tend to match the present state.

Accordingly, a technology which is intended for poor quality coals and by which coal to be used is incinerated in advance, the obtained coal ash is sintered, a conglutination degree of the sintered ash is measured and adhesion of ash is predicated and evaluated is being developed as disclosed in patent literature 1. However, sinterability and fusibility of ash is largely affected not only by temperature, but also by an ambient gas composition. In the case of a reducing atmosphere with a high concentration of a reducing gas such as CO or H2, the softening point and melting point of the ash decrease and it becomes easier to sinter. Further, in the case of an oxidizing atmosphere, the softening point and melting point of the ash increase and it becomes more difficult to sinter. Thus, the technology of patent literature 1 that does not take into consideration the ambient gas composition has a problem of having difficulty in accurately predicting adhesion of ash in a boiler.

CITATION LIST

Patent Literature

[Patent literature 1] Japanese Unexamined Patent Publication No. 2004-361368 [Non-Patent Literature]
[Non-Patent Literature 1] "Understanding slagging and fouling during pf combustion (IEACR/72), written by Gordon Couch, August 1994

SUMMARY OF INVENTION

Technical Problem

In order to stably operate a boiler using various types of solid fuels including poor quality coals, the present invention aims to provide a method for suppressing adhesion of ash and a device for suppressing adhesion of ash in a boiler, which can suppress adhesion of ash by accurately predicting adhesion of ash in the boiler

Solution to Problem

The present invention is directed to a method for suppressing adhesion of ash in a boiler, including: a step of determining a mix ratio of a plurality of types of fixed fuels, based on a composition of an ash constituent preliminarily measured for each of the plurality of types of solid fuels, and based on a slag ratio that is calculated for each of the plurality of types of solid fuels, and indicates a ratio of a part of a specific amount of an ash constituent which becomes slag under a predetermined ambient temperature and a predetermined ambient gas composition, so that slag ratios in the boiler are not more than reference values; and a step of mixing the plurality of types of solid fuels based on the mix ratio of the plurality of types of fixed fuels, and supplying the mixture as a fuel to the boiler.

The present invention is also directed to a device for suppressing adhesion of ash in a boiler, including: a calculating unit for calculating a slag ratio for each of a plurality of types of solid fuels, the slag ratio indicating a ratio of a part of a specific amount of an ash constituent which becomes slag under a predetermined ambient temperature and a predetermined ambient gas composition, and determining, based on a composition of an ash constituent measured in advance for each of the plurality of types of solid fuels, a mix ratio of the plurality of types of fixed fuels so that the slag ratios in the boiler are not more than reference values; and a fuel supply amount adjusting unit for adjusting a supply amount of the plurality of types of solid fuels based on the mix ratio of the plurality of types of fixed fuels.

As seen from the above, the present invention focuses on slag that is a composition melted by being burned in the boiler, is suspended in a combustion air stream in the boiler and deposits on furnace walls and heat exchanger tube banks. In the present invention, the mix ratio of the plurality of types of solid fuels is determined based on the slag ratio calculated for each solid fuel and the composition of the ash constituent. Accordingly, by evaluating an ash adhesion property based on the slag ratio as an evaluation index newly built in the present invention and determining the mix ratio of the plurality of types of solid fuels so that the slag ratios are not more than the reference values, adhesion of ash can be suppressed. Here, the solid fuels include coals, sludge carbides, biomass fuels and the like. Further, since the amount of heat is weighted heavily in the boiler, the supply amount of the solid fuels that become a fuel is so determined that the amount of heat introduced to the boiler is constant.

Here, in the method and device for suppressing adhesion of ash in a boiler according to the present invention, the slag ratio may be calculated by thermodynamic equilibrium calculation based on the composition of the ash constituent, or calculated based on slag measured when each of the plurality of solid fuels is heated at a predetermined ambient temperature and a predetermined ambient gas composition.

In the case of calculating the slag ratio by thermodynamic equilibrium calculation based on the composition of the ash constituent, the slag ratio can be obtained without carrying out any experiment. Further, in the case of calculating the slag ratio based on the slag measured in advance for each of the plurality of types of solid fuels and produced by heating under the predetermined ambient temperature and ambient gas composition, the slag ratio matching an actual condition of the boiler can be obtained.

Further, in the method and device for suppressing adhesion of ash in a boiler according to the present invention, the reference values may be determined based on an ash deposition ratio relative to the slag ratio so as to reduce the ash deposition ratio; the ash deposition ratio may be calculated as a ratio of an actual amount, preliminarily investigated, of deposited ash relative to an amount of ash colliding with an ash adhesion probe inserted into the boiler; and the amount of colliding ash may be obtained from supply amounts and ash contents of the solid fuels and the shape of a furnace of the boiler, and calculated as the total amount of ash constituents colliding with a projected area of the ash adhesion probe.

According to this, adhesion of ash can be suppressed by determining the reference values of the slag ratio so as to reduce the ash deposition ratio based on a comparison result between the ash deposition ratio investigated in advance and the slag ratio.

Further, in the method and device for suppressing adhesion of ash in a boiler according to the present invention, the reference values may be determined to be 50 to 60 wt % so that the ash deposition ratio is not more than 5 to 7 wt %.

According to this, if the slag ratio is in the range of 50 to 60 wt % based on the comparison result between the ash deposition ratio investigated in advance and the slag ratio, the ash deposition ratio is reduced to 5 to 7 wt % or less, and adhesion of ash can be suppressed.

Here, in the method for suppressing adhesion of ash in a boiler according to the present invention, the predetermined ambient temperature and predetermined ambient gas composition may be an ambient temperature and an ambient gas composition near a burner.

Further, in the device for suppressing adhesion of ash in a boiler according to the present invention, a measuring unit for measuring a temperature and an ambient gas composition in a boiler combustion chamber may be further provided, and the predetermined ambient temperature and predetermined ambient gas composition may be a temperature and an ambient gas composition, measured by the measuring unit, in the boiler combustion chamber.

According to this, the slag ratio in ash in each part in the boiler can be properly obtained and an appropriate mix ratio of the plurality of types of solid fuels can be calculated.

Further, in the method and device for suppressing adhesion of ash in a boiler according to the present invention, the predetermined ambient temperature and predetermined ambient gas composition may be a highest ambient temperature on the design of the boiler and an ambient gas composition in a part having the highest ambient temperature, or an ambient gas composition having a highest degree of reduction on the design of the boiler and a temperature in a part having the highest degree of reduction.

According to this, an appropriate mix ratio of the plurality of types of solid fuels can be calculated independently of the state of the boiler. Note that the ambient gas composition having the highest degree of reduction on the design of the boiler means an ambient gas composition having a highest concentration of a reducing gas such as CO or $H_2$.

Effect of Invention

According to the method and device for suppressing adhesion of ash in a boiler of the present invention, adhesion of ash in the boiler can be accurately predicted and suppressed in the boiler using various types of solid fuels including poor quality coals. Therefore, the boiler can be stably operated.

EMBODIMENT OF INVENTION

Hereinafter, an embodiment of a method and a device for suppressing adhesion of ash in a boiler according to the present invention is described for one specific example with reference to the drawings. Note that the following description is merely illustrative and does not show a limitation of the application of the method and device for suppressing adhesion of ash in a boiler according to the present invention. That is, the method and device for suppressing adhesion of ash in a boiler according to the present invention are not limited to the following embodiment and various changes can be made without departing from the scope as claimed.

Figure 1:
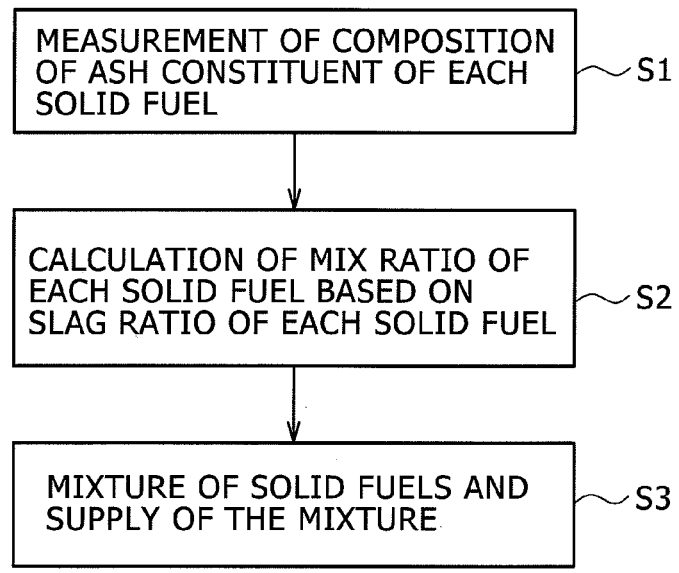
FIG. 1 is a step diagram showing a procedure of a method for suppressing adhesion of ash in a boiler according to a present embodiment.

First, an example of a method for suppressing adhesion of ash in a boiler according to the present embodiment is described based on FIG. 1. FIG. 1 is a step diagram showing a procedure of the method for suppressing adhesion of ash in a boiler according to the present embodiment.

In the method for suppressing adhesion of ash in a boiler according to this embodiment, a composition of an ash constituent of each solid fuel planned to be used in a boiler is first measured (Step S1), as shown in FIG. 1. A coal property of the solid fuel such as water content, calorific value, ash content or a composition of the ash constituent is measured as the composition of the ash constituent. Here, the solid fuels include coals, sludge carbides, biomass fuels and the like.

Subsequently, a mix ratio of each solid fuel is calculated based on a slag ratio of each solid fuel (Step S2). The slag ratio is an evaluation index of an ash adhesion property used in this embodiment and means a ratio of a part of a specific amount of a solid ash constituent which becomes slag under a specific temperature and an ambient condition. Further, the slag means a component which is melted by combustion, is suspended in a combustion air stream in the boiler and deposits on furnace walls and heat exchanger tube banks. The slag ratio is calculated for each solid fuel and mixing conditions of each solid fuel. Here, the slag ratio is obtained by calculating, using thermodynamic equilibrium calculation, a composition and a phase in a state where the ash constituent, measured in advance, of each solid fuel is thermodynamically most stable under specific conditions (temperature, ambient gas composition), i.e. in a state where Gibbs free energy (ΔG) is almost zero. Note that the method for calculating the slag ratio is not limited to the above method, and the ash of each solid fuel may be heated and the slag ratio at each temperature and ambient gas composition may be measured in advance. By this, the slag ratio matching an actual condition of the boiler can be obtained.

Then, in order to evaluate the slag ratio as the evaluation index of the ash adhesion property used in this embodiment, an ash deposition ratio is calculated. Here, the ash deposition ratio is a ratio of the amount of ash deposited on an ash adhesion probe, inserted into the furnace of the boiler, to the amount of ash colliding with the ash adhesion probe, means easiness of deposition of ash and is expressed by the following equation. Note that the amount of ash colliding with the ash adhesion probe is the total amount of ash constituents colliding with a projected area of the ash adhesion probe and obtained from the supply amount and ash contents of the solid fuels and the furnace shape of the boiler.

$$\text{Ash deposition ratio[wt \%]} = (\text{amount of deposited ash[kg]})/(\text{amount of ash colliding with ash adhesion probe [kg]}) \cdot 100 \quad \text{[Equation 1]}$$

Note that calculation and evaluation of the ash deposition ratio need not be carried out in the actual boiler and may be carried out in a combustion test furnace or a drum boiler.

In this way, a value (reference value) of the slag ratio at which the ash deposition ratio is reduced to about 5 to 7 wt % is determined based on a relationship between the ash deposition ratio measured in advance and the slag ratio. The mix ratio of the respective solid fuels is used as a parameter, and a composition of an ash constituent of the mixed fuel is calculated from the compositions of the ash constituents, measured in Step S1, of the respective solid fuels. The slag ratio in the ash is obtained by thermodynamic equilibrium calculation. Then, the mix ratio of the respective solid fuels is calculated to obtain an ash composition that the slag ratio in the ash is not more than the determined reference value. Here, the supply amount of the solid fuels to become a fuel is determined so that the amount of heat introduced to the boiler is constant. Note that, in thermodynamic equilibrium calculation, the ambient temperature and the ambient gas composition near the burner where adhesion of ash to the boiler wall notably occurs are used. Further, thermodynamic equilibrium calculation is not only carried out based on the ambient temperature and the ambient gas composition near the burner, but also may be carried out based on the ambient temperature and the ambient gas composition in a desired part such as the heat exchanger tube bank, on which ash are likely to deposit. In this way, the slag ratio in ash can be properly obtained for each part in the boiler, and an appropriate mix ratio of a plurality of types of solid fuels can be calculated. Further, thermodynamic equilibrium calculation is not limited to the above calculation and may be carried out based on a highest ambient gas temperature on the design of the boiler and an ambient gas composition in a part having the highest ambient gas temperature. Further, thermodynamic equilibrium calculation may also be carried out based on an ambient gas composition having a highest degree of reduction (concentration of a reducing gas such as CO or $H_2$ is highest) on the design of the boiler and a temperature in a part having the highest ambient gas composition. By doing so, the mix ratio of the plurality of types of solid fuels can be determined independently of the combustion temperature in the furnace of the boiler.

Although the slag ratio as the evaluation index of the ash adhesion property is evaluated based on the ash deposition ratio in this embodiment, evaluation is not limited to this. A combustion test may be carried out for various ratios of slag contained in a fuel using a combustion test furnace or a drum boiler, and a slag ratio when a mass of clinker (melted slag) of a size, which cannot be unloaded by a conveyor installed in the boiler, falls down on a furnace wall may be used as a reference value to evaluate the slag ratio. Alternatively, a slag ratio when a main steam temperature/main steam pressure deviates from a specified region or varies may be used as a reference value to evaluate the slag ratio.

Finally, the solid fuels are mixed based on the mix ratio, calculated in Step S2, of the respective solid fuels, and these solid fuels are crushed and supplied as a fuel to the boiler (Step S3).

Figure 2:
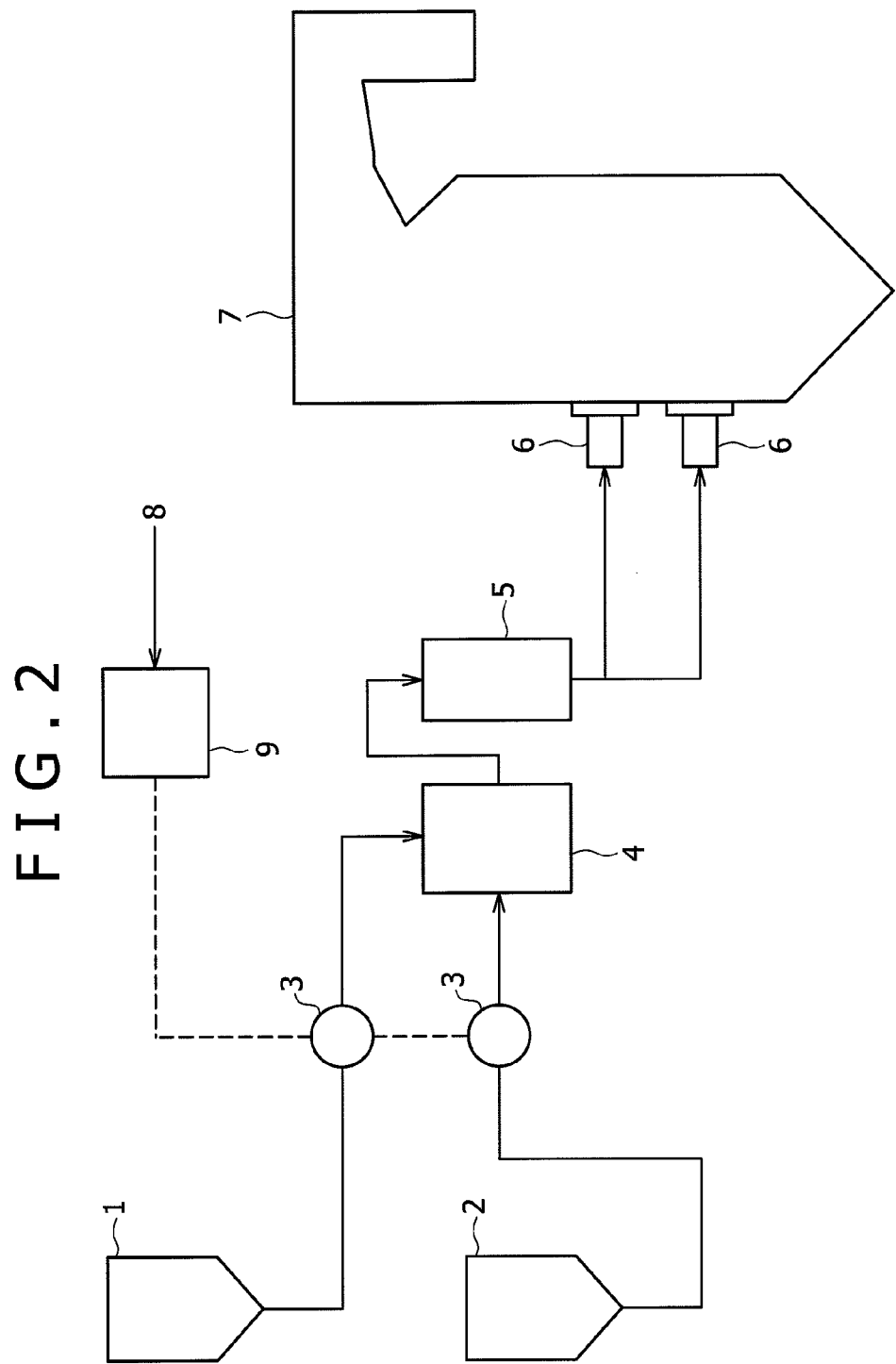
FIG. 2 is a schematic diagram showing a device for suppressing adhesion of ash in a boiler according to the present embodiment.

Next, an example of a device for suppressing adhesion of ash in a boiler according to the present embodiment is described based on FIG. 2. FIG. 2 is a schematic diagram showing the device for suppressing adhesion of ash in a boiler according to the present embodiment.

As shown in FIG. 2, a boiler 7 includes hoppers 1, 2, fuel supply amount adjusting devices (fuel supply amount adjusting units) 3, a mixer 4, a crusher 5, burners 6 and a calculator (calculating unit) 9. The device for suppressing adhesion of ash in a boiler according to the present embodiment is composed of the fuel supply amount adjusting devices 3 and the calculator 9.

The hoppers 1, 2 respectively store two types of solid fuels having different ash properties. Here, the solid fuels include coals, sludge carbides, biomass fuels and the like. Note that, although two hoppers are shown in FIG. 2, the number of the hoppers is arbitrary without being limited to this. The fuel supply amount adjusting devices 3 adjust the amounts of the solid fuels, fed from the hoppers 1, 2, based on a mix ratio of the solid fuels calculated by the calculator 9 to be described later. The mixer 4 mixes the solid fuels cut and fed by the fuel supply amount adjusting devices 3. The crusher 5 crushes the solid fuel, which has been mixed in the mixer 4, into pulverized coal. The burners 6 burn the pulverized coal blown thereto together with air. The boiler 7 burns the pulverized coal and collects heat. Although not shown, the boiler includes a furnace that burns supplied fuel with the burners 6 and the like and generates heat, and heat exchanger tube banks arranged from an upper part of the furnace toward a downstream side and adapted to carry out heat exchange by allowing a combustion gas to flow inside. Here, the combustion gas discharged from the boiler is exhausted from a chimney. Further, the heat exchange tube banks are composed of an upper heat transfer unit including a secondary heater, a tertiary heater, a final heater and a secondary reheater arranged side by side at predetermined intervals in an upper part of the furnace and a rear heat transfer unit including a primary heater, a primary reheater and a coal economizer arranged in a rear part of the furnace.

The calculator 9 preliminarily collects properties of the solid fuels such as water contents, calorific values, ash contents, compositions of ash constituents, as data 8. The calculator 9 uses the mix ratio of the solid fuels as a parameter, and calculates the composition of the ash constituent of the mixed fuel from the compositions of the ash constituents of the respective solid fuels measured in advance. Then, the calculator 9 determines a value (reference value) of the slag ratio, at which the ash deposition ratio is reduced to about 5 to 7 wt %, from the relationship between the ash deposition ratio measured in advance and the slag ratio. Finally, the calculator 9 determines the mix ratio of the respective solid fuels to obtain an ash composition such that the slag ratio obtained by thermodynamic equilibrium calculation is not more than the determined reference value. Here, the supply amount of the solid fuels to become a fuel is determined so that the amount of heat introduced to the boiler is constant. Note that the slag ratio is the evaluation index of the ash adhesion property used in this embodiment and means a ratio of a part of a specific amount of a solid ash constituent which becomes slag under a specific temperature and a specific ambient condition. The ash deposition ratio, the slag ratio and the relationship of these are as described above and not described here.

Further, the ambient temperature and the ambient gas composition near the burners where adhesion of ash to the boiler wall notably occurs, for example, are used in thermodynamic equilibrium calculation. The ambient temperature and the ambient gas composition near the burners are measured using an unillustrated measuring device (measuring unit) disposed near the burners. Note that the measuring device is not only disposed in the vicinity of the burners. A measuring device may be disposed in a desired part such as at the heat exchanger tube bank, where adhesion of ash is likely to occur, and thermodynamic equilibrium calculation may be carried out based on an ambient temperature and an ambient gas composition in such a part. By this, the slag ratio in ash in each part in the boiler can be properly obtained and an appropriate mix ratio of a plurality of types of solid fuels can be calculated. Further, thermodynamic equilibrium calculation is not limited to the above calculation and may be carried out based on a highest ambient gas temperature in the design of the boiler and an ambient gas composition in a part having the highest ambient gas temperature. Further, thermodynamic equilibrium calculation may also be carried out based on an ambient gas composition having a highest degree of reduction (concentration of a reducing gas such as CO or H2 is highest) and a temperature in a part having the highest ambient gas composition. By this, the mix ratio of the plurality of types of solid fuels can be determined independently of the combustion temperature in the furnace of the boiler.

Further, a mix ratio of solid fuels is not only calculated based on ratios of slag obtained by thermodynamic equilibrium calculation, but may also be calculated based on ratios of slag measured in advance when the ash constituents of the respective solid fuels are heated. By this, the slag ratio matching an actual condition of the boiler can be obtained.

As just described, the method and device for suppressing adhesion of ash in a boiler of the present embodiment focus on slag which is a composition melted by being burned in the boiler, is suspended in a combustion air stream in the boiler and deposits on the furnace walls and the heat exchanger tube banks. The mix ratio of the plurality of types of solid fuels is determined based on the slag ratio calculated for each solid fuel and the composition of the ash constituent. By evaluating the ash adhesion property based on the slag ratio as the evaluation index newly built in the present invention and determining the mix ratio of the plurality of types of solid fuels so that the slag ratio is not more than the reference value in this way, adhesion of ash in the boiler can be accurately predicted and suppressed. Further, the supply amount of the solid fuels to become a fuel is determined so that the amount of heat introduced to the boiler is constant, whereby the amount of heat weighted heavily in the boiler is considered.

EXAMPLE

Figure 3:
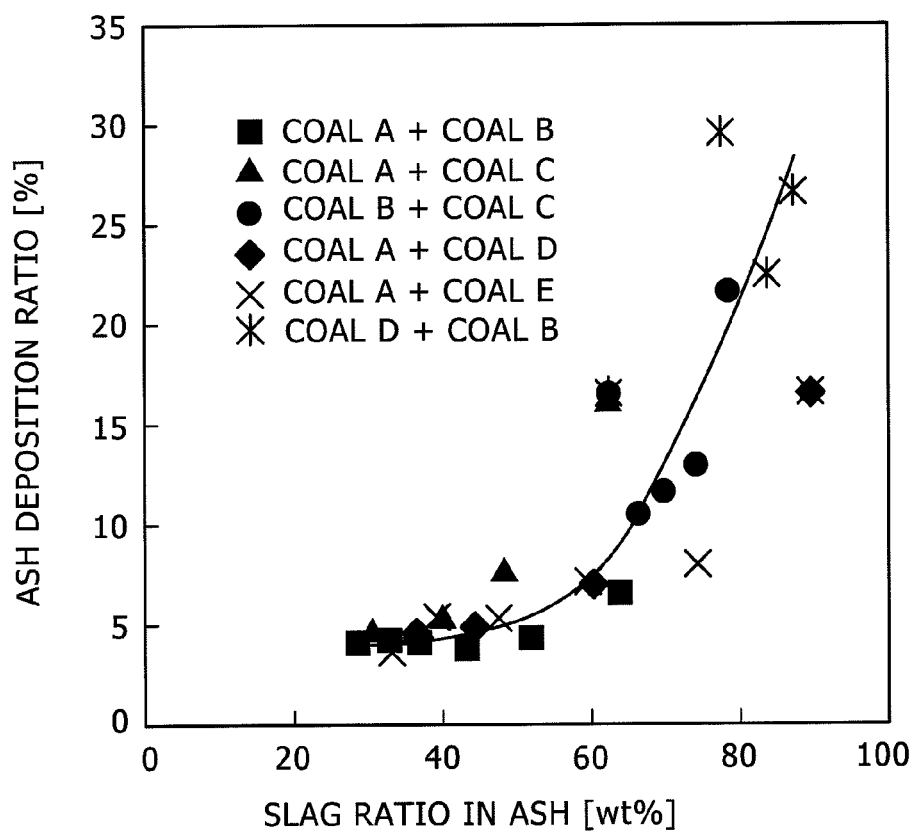
FIG. 3 is a graph showing a relationship between slag ratio and ash deposition ratio according to a present example.

Next, an example of the method and device for suppressing adhesion of ash in a boiler is described based on FIG. 3 and Table 1. FIG. 3 is a graph showing a relationship between slag ratio and ash deposition ratio according to this example. Table 1 is a table showing properties of coals used in the present example.

In the present example, an experiment was carried out using five types of pulverized coals having different compositions of ash constituents under a condition that a total calorific value of city gas introduced for heating was constant at 149 kW in a pulverized coal combustion test furnace (furnace inner diameter of 400 mm, in-furnace effective height of 3650 mm). In the experiment, the supply amount of pulverized coals was adjusted by introducing five types of pulverized coals individually or as a mixture of a plurality of types of pulverized coals so that the calorific value of the introduced pulverized coals is constant at 60 kW. Then, the pulverized coals, the supply amount of which was adjusted, were burned together with combustion air by a burner provided at the top of the furnace, an ash adhesion probe was inserted in a lower part and held for 100 minutes, and the deposit ratio of ash deposited on the surface of the ash adhesion probe was investigated. Here, an in-furnace ambient temperature in the part where the ash adhesion probe was inserted is about 1300° C. similar to a temperature at which an ash adhesion phenomenon occurs in a drum boiler. Further, the interior of the ash adhesion probe is water-cooled and temperature-regulated so that the surface temperature of the ash adhesion probe is about 500° C. The properties of the five types of pulverized coals used in the experiment are shown in Table 1.

TABLE 1

|  | Coal A | Coal B | Coal C | Coal D | Coal E |
|---|---|---|---|---|---|
| Ash content [wt %-DB] | 12.53 | 6.23 | 1.76 | 2.73 | 5.5 |
| $SiO_2$ [wt %-ash] | 69.8 | 56.9 | 40 | 52 | 53 |
| $Al_2O_3$ [wt %-ash] | 20.73 | 23 | 27.85 | 20.3 | 23.5 |
| CaO [wt %-ash] | 0.48 | 2.19 | 3.7 | 6.03 | 3.1 |
| $TiO_2$ [wt %-ash] | 1.03 | 0.57 | 0.56 | 1.08 | 1 |
| $Fe_2O_3$ [wt %-ash] | 4.95 | 11.8 | 19.95 | 12.1 | 9 |
| MgO [wt %-ash] | 0.66 | 2.27 | 1.21 | 1.9 | 2.7 |
| $Na_2O$ [wt %-ash] | 0.25 | 0.04 | 0.14 | 0.39 | 0.6 |
| $K_2O$ [wt %-ash] | 0.98 | 0.44 | 0.4 | 0.67 | 2.1 |
| $P_2O_5$ [wt %-ash] | 0.2 | 0.34 | 0.05 | 0.13 | 0.36 |
| MnO [wt %-ash] | 0.05 | 0.03 | 0.27 | 0.06 | 0.2 |
| $V_2O_5$ [wt %-ash] | 0.05 | 0.05 | 0.05 | 0.02 | 0 |
| $SO_3$ [wt %-ash] | 0.4 | 1.27 | 3.8 | 5.24 | 4.6 |

Based on the properties of the pulverized coals shown in Table 1, a composition and a phase in a state where a specific amount of an ash constituent is thermodynamically most stable under specific conditions (temperature, ambient gas composition), i.e. in a state where Gibbs free energy (AG) is almost zero are calculated by thermodynamic equilibrium calculation. By this, the slag ratio of the pulverized coal used as a fuel in the experiment is calculated. In the present example, thermodynamic equilibrium calculation was carried with a temperature of 1300° C. and an ambient gas composition of $O_2$: 1 vol %, $CO_2$: 19 vol % and $N_2$: 80 vol %. FIG. 3 shows the relationship between the slag ratio and the ash deposition ratio according to the present example.

As shown in FIG. 3, in the present example, the ash deposition ratio is about 5 to 7 wt % or less until the slag ratio is 50 to 60 wt %. It is clear from FIG. 3 that the ash deposition ratio suddenly increases when the slag ratio becomes more than 50 to 60 wt %. It can be understood from this that adhesion of ash can be suppressed by adjusting the mix ratio of the five types of pulverized coals so that the slag ratio calculated according to the composition of the ash constituent is not more than 50 to 60 wt %.

Although the embodiment of the present invention has been described above, the present invention is not limited to the above embodiment and various changes can be made without departing from the scope as claimed. The present application is based on Japanese Patent Application (No. 2009-170771) filed on Jul. 22, 2009, and the contents of which are hereby incorporated by reference.

REFERENCE SIGNS LIST 3 fuel supply amount adjusting device (fuel supply amount adjusting unit)
7 boiler
9 calculator (calculating unit)

The invention claimed is:

1. A method for suppressing adhesion of ash in a boiler, comprising:
a step of determining a mix ratio of a plurality of types of fixed fuels, based on a composition of an ash constituent preliminarily measured for each of the plurality of types of solid fuels, and based on a slag ratio that is calculated for each of the plurality of types of solid fuels, and indicates a ratio of a part of a specific amount of an ash constituent which becomes slag under a predetermined ambient temperature and a predetermined ambient gas composition, so that slag ratios in the boiler are not more than reference values; and
a step of mixing the plurality of types of solid fuels based on the mix ratio of the plurality of types of fixed fuels, and supplying the mixture as a fuel to the boiler.

2. The method for suppressing adhesion of ash in a boiler according to claim 1, wherein the slag ratio is calculated by thermodynamic equilibrium calculation based on the composition of the ash constituent, or calculated based on slag measured when each of the plurality of solid fuels is heated at a predetermined ambient temperature and a predetermined ambient gas composition.

3. The method for suppressing adhesion of ash in a boiler according to claim 1, wherein:
the reference values are determined based on an ash deposition ratio relative to the slag ratio so as to reduce the ash deposition ratio;
the ash deposition ratio is calculated as a ratio of an actual amount, preliminarily investigated, of deposited ash relative to an amount of ash colliding with an ash adhesion probe inserted into the boiler; and
the amount of colliding ash is obtained from supply amounts and ash contents of the solid fuels and the shape of a furnace of the boiler, and calculated as the total amount of ash constituents colliding with a projected area of the ash adhesion probe.

4. The method for suppressing adhesion of ash in a boiler according to claim 1, wherein the reference values are determined to be 50 to 60 wt % so that the ash deposition ratio is not more than 5 to 7 wt %.

5. The method for suppressing adhesion of ash in a boiler according to claim 1, wherein the predetermined ambient temperature and predetermined ambient gas composition are an ambient temperature and an ambient gas composition near a burner.

6. The method for suppressing adhesion of ash in a boiler according to claim 1, wherein the predetermined ambient temperature and predetermined ambient gas composition are a highest ambient temperature on the design of the boiler and an ambient gas composition in a part having the highest ambient temperature, or an ambient gas composition having a highest degree of reduction on the design of the boiler and a temperature in a part having the highest degree of reduction.

* * * * *